(12) United States Patent
Sholupov

(10) Patent No.: US 8,358,409 B2
(45) Date of Patent: Jan. 22, 2013

(54) ATOMIC ABSORPTION MERCURY ANALYZER

(75) Inventor: Sergey Evgenyevich Sholupov, St. Petersburg (RU)

(73) Assignee: Lumex Instruments Limited, Pallouriotissa, Nicosia (CY)

( * ) Notice: Subject to any disclaimer, the term of this patent is extended or adjusted under 35 U.S.C. 154(b) by 204 days.

(21) Appl. No.: 12/922,818

(22) PCT Filed: May 18, 2009

(86) PCT No.: PCT/RU2009/000254
§ 371 (c)(1),
(2), (4) Date: Sep. 15, 2010

(87) PCT Pub. No.: WO2009/145669
PCT Pub. Date: Dec. 3, 2009

(65) Prior Publication Data
US 2011/0026020 A1    Feb. 3, 2011

(30) Foreign Application Priority Data
May 26, 2008    (RU) ................. 2008121928

(51) Int. Cl.
*G01J 3/30* (2006.01)
*H01J 17/20* (2012.01)
*H01J 61/20* (2006.01)
(52) U.S. Cl. ........................ 356/313; 313/639
(58) Field of Classification Search .................. 356/313; 313/621, 639, 637, 638, 571, 573
See application file for complete search history.

(56) References Cited

U.S. PATENT DOCUMENTS 2,118,452 A * 5/1938 Le Bel .......................... 315/248
3,811,778 A * 5/1974 Hadeishi ....................... 356/312
6,657,390 B2 * 12/2003 Serizawa et al. ............. 313/642

FOREIGN PATENT DOCUMENTS

| DE | 4411441 A1 | 10/1995 |
| EP | 0400513 A2 | 12/1990 |
| RU | 2038581 C1 | 6/1995 |
| RU | 6906 U1 | 6/1998 |

OTHER PUBLICATIONS

T. Hadeishi et. al., Mercury Monitor for Ambient Air, Apr. 19, 1973, Science, vol. 187, pp. 348-349.*

* cited by examiner

Primary Examiner — Gregory J Toatley
Assistant Examiner — Shawn DeCenzo
(74) Attorney, Agent, or Firm — Christopher L. Parmelee; Walker & Jocke

(57) ABSTRACT

The invention relates to analytical chemistry. In the analyser, mercury placed in a spectral lamp is enriched with a mercury isotope having an even neutron number, wherein said isotope constitutes not less than 50% of the total mercury content in the spectral lamp. Moreover, the discharge cavity of the spectral lamp is connected to a ballast cavity, the volume of which is greater than the discharge cavity volume, and electrical discharge generating means, the discharge cavity and the ballast cavity are designed in such a way that the discharge generated in the discharge cavity does not penetrates into the ballast cavity. A buffer gas in the spectral lamp contains a noble gas in a quantity equal to or greater than 50%, the charge of the atomic core of said gas being not less than 36. Said invention makes it possible to lower the detection level of mercury in a carrier gas and to reduce a drift.

3 Claims, 5 Drawing Sheets

ATOMIC ABSORPTION MERCURY ANALYZER

The claimed invention refers to analytical chemistry, in particular to spectral atomic absorption analysis with a differential technique of measurement of mercury concentration and can be used for considerable reduction of the mercury detection limit in a carrier gas and reduction of drift.

There is an atomic absorption mercury analyzer with Zeeman correction of background absorption HGG-3 Scintrex, Canada (2) containing a spectral mercury lamp placed in the pulsed magnetic field and shaped as a capillary, with electrodes for electrical discharge excitation welded into its ends, a lens, a light beam splitter, an analytical cell, photo detectors of the analytical and reference channels. When strength of the magnetic field is zero the optical density of mercury atoms and background absorption is measured. When strength of the magnetic field has working value the optical density of background absorption only is measured as the Zeeman components of the emission resonance line of mercury are shifted by the magnetic field and are beyond the absorption line envelope. The difference between these two measurements provides the value of the optical density of mercury atoms related to the mercury concentration by the calibration expression.

The drawbacks of the analogues are the high detection limit of mercury in the air (160 ng/m$^3$), narrow dynamic range of measurements (two orders of magnitude), the weight and energy consumption are too large for portable analyzers.

The closest analyzer to the proposed invention in terms of technical essence is the atomic absorption mercury analyzer with Zeeman correction of background absorption (1) consisting of a photo detector, an analytical cell, an inclined plate, a modulator of radiation polarization and a spectral lamp placed between the poles of the magnet. This technique implements the method of differential atomic absorption spectroscopy (DAAS). During observation along the lines of magnetic force only σ-components of the Zeeman triplet are detected, with one σ-component being in the area of the maximum of the absorption line and performing the role of the analytical line and the other being at the edge of the absorption line envelope, where the absorption cross section is much less than in the maximum and performing the role of the reference line. In the processing block two signals on the first and second harmonics of modulation frequency are selected: the first one is proportional to concentration of mercury atoms in the analytical cell and the second one is proportional to the full intensity of σ-components. Further processing of the signals occurs in the microprocessor according to the known algorithm [1].

The drawbacks of the prototype include the high detection limit of mercury concentration in the atmospheric air (30 ng/m$^3$ with the response time of the device of 5 seconds) and the large zero-level drifts.

The task of the invention is creation of an atomic absorption mercury analyzer with improved analytical characteristics, namely with the low detection limit and low drift value.

The set task is achieved by the atomic absorption mercury analyzer including optically coupled a photo detector, analytical cell, a modulator of radiation polarization and a spectral lamp containing a discharge cavity located between the poles of the magnet and bound to the means of electrical discharge excitation, with buffer gas and mercury placed in the spectral lamp; the mercury placed in the spectral lamp is enriched with mercury isotope with an even number of neutrons and the isotope makes at least 50% of the total quantity of mercury in the spectral lamp.

The atomic absorption mercury analyzer also contains a ballast cavity that is connected with the discharge cavity and its volume exceeds the volume of the discharge cavity. The means of electrical discharge excitation, the discharge cavity and the ballast cavity are embodied with the possibility of excitation of a discharge in the discharge cavity that does not penetrate into the ballast cavity.

In addition to that, the buffer gas in the spectral lamp contains at least 50% of inert gas, the charge of its atomic nucleus being at least 36.

The essence of the invention is that the detection limit and the drift are reduced due to the use of mercury in the spectral lamp that is enriched with isotope for which the value of differential cross section of absorption of resonance radiation is much higher than in case of use of mercury with natural composition in the spectral lamp. In fact, in DAAS the optical density of absorbing atoms D is measured (D=ΔQnL, where ΔQ—the differential cross section of resonance radiation, n—the density of the atoms specified, L—the length of the absorbing layer), from which the density n of the atoms specified is then calculated.

By definition the detection limit is the concentration (in case of DAAS it is the optical density) that exceeds the noise level σ in three times, $$D_{DL}=\Delta Q n_{DL} L=3\sigma.$$

As the noise level is determined by parameters of the spectral lamp and the measuring system and does not depend on the differential cross section of absorption, the increase of the latter results in reduction of the detection limit, which follows from the expression given above. The drift value is reduced in a similar way at increase of the differential cross section of absorption as drift is noise in the ultra-low frequency range that is also determined only by the parameters of the spectral lamp and measuring system and does not depend on the differential cross section of absorption.

The spectral lamp has two different areas—a ballast cavity that is a reservoir for mercury vapor and a discharge cavity in which the electrical discharge is excited. It allows to stabilize the pressure of mercury vapor in the gas phase inside the spectral lamp, that stabilizes radiation transfer and self-absorption of resonance radiation inside the spectral lamp and thus reduces the drift value.

Besides, when heavy inert gases with the atomic nucleus charge of at least 36, e.g. Kr or Xe, as a buffer gas in the spectral lamp is used, then the intensity of resonance radiation is increased at the same supplied power, that reduces the noise level (in our case, the shot noise is the dominant one) and the detection level is, correspondingly, reduced.

BRIEF DESCRIPTION OF THE SEVERAL VIEWS OF THE DRAWINGS

The essence of the claimed invention is illustrated by drawings:

DETAIL DESCRIPTION OF THE INVENTION

Figure 1:
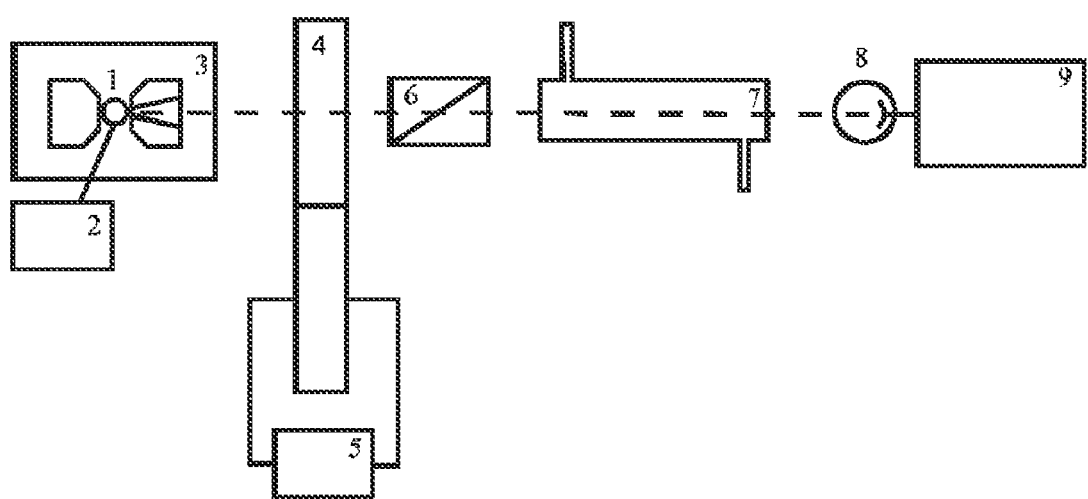
FIG. 1. Flow chart of the analyzer.

The flow chart of the atomic absorption mercury analyzer given in FIG. 1 consists of the spectral lamp 1, means of electrical discharge excitation 2, the magnet 3, the modulator of radiation polarization consisting of an optical-acoustic modulator 4 with a quartz generator 5 and a polarizer 6, the analytical cell 7, the photo detector 8 as well as the block of signal processing 9.

Mercury resonance radiation (254 nm or 185 nm) can be selected by using a distributed spectral filter implemented on mirrors (not shown in the drawing) and a photo detector or a discrete intereference filter.

The means of electrical discharge excitation 2 can be implemented in the form of electrodes connected with the high-frequency exciting generator and installed on the discharge cavity of the spectral lamp.

The analytical cell 7 can be implemented in the form of an enclosed volume where the analyzed gas is introduced and removed through gas nozzles and where the probe radiation is introduced and removed through quartz windows. The analytical cell 7 can have an open embodiment, with no windows, for example. In this case the input gas nozzle will be installed in the center of the analytical cell while the probe radiation will pass the analytical volume. The analyzed gas enters through the inlet nozzle into the analytical volume and freely leaves it through the end holes in the cell. Such an embodiment of the analytical cell allows to avoid contamination of windows with various admixtures being in the analyzed gas. Another embodiment of the open analytical cell is lack of both windows and walls of the cell. In this case the analyzer is placed in the analyzed gas, the atmospheric air, for example, that enters in the zone of probe radiation due to convective exchange. The advantages of this technique of measurement are lack of memory effects, there is no need for a pump, which is quite important for portable mercury analyzers.

The magnet is made from a material with a high remanent magnetization in the form of two discs parted by a separator. The discharge cavity of the spectral lamp 1 is set in the gap between the discs. The discs are magnetized so that into the gap one disc has the southern pole and the other disc—the northern pole. For coupling radiation out of the spectral lamp 1 one of the discs has a hole that allows to extract the radiation along the lines of magnetic force towards the optical axis.

Figure 5:
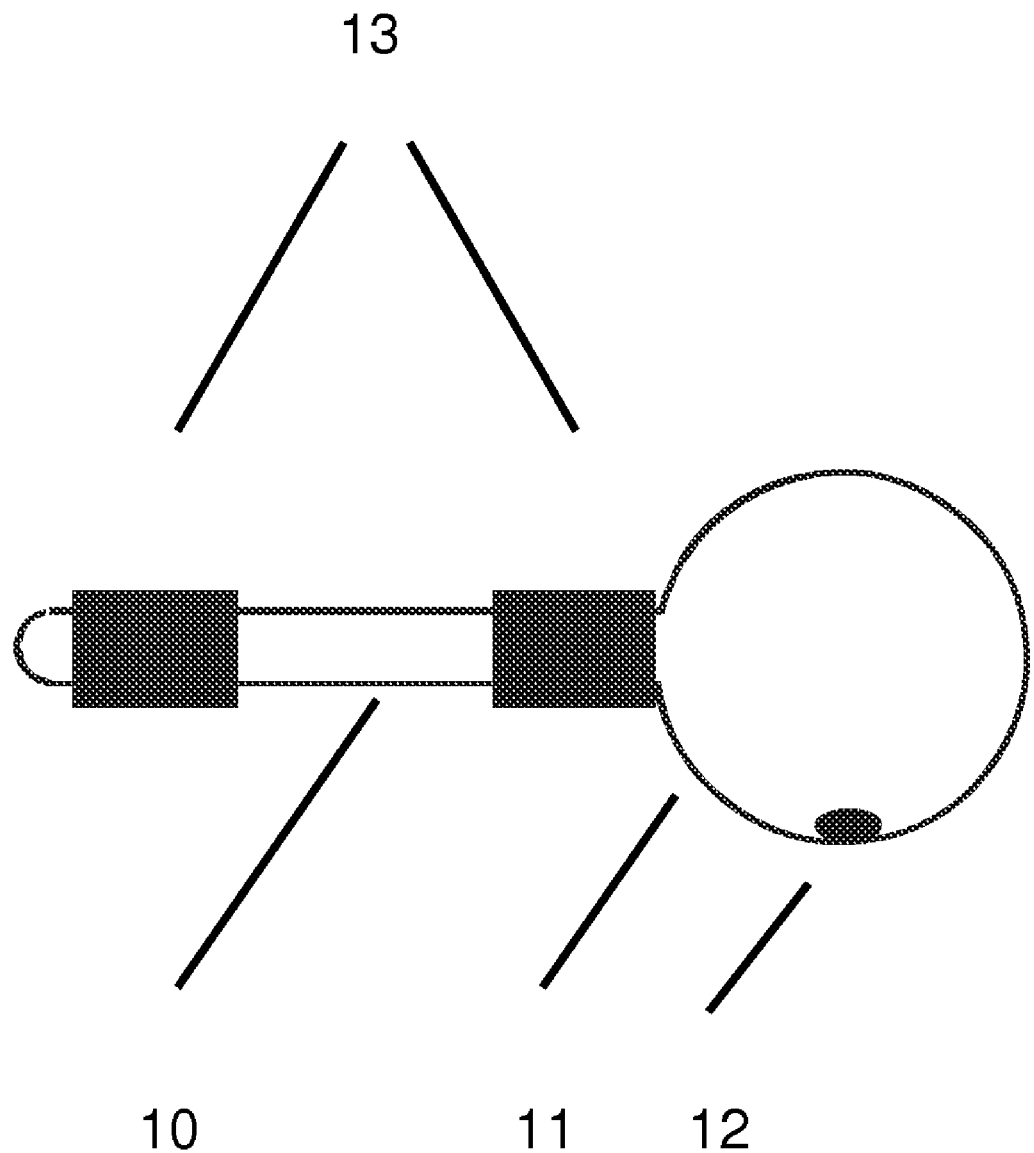
FIG. 5. Design of the spectral lamp: 10—discharge cavity, 11—ballast cavity, 12—metal mercury drop, 13—electrodes for electrical discharge excitation.

The spectral lamp 1 (FIG. 5) mechanically consists of two parts: the discharge cavity 10 in the form of a capillary and the ballast cavity 11 in the form of a spherical bulb. These two quartz parts are welded together so that their internal areas form a single enclosed cavity. On the ends of the capillary there are external electrodes 13 to which the voltage of the exciting generator is supplied. The low potencial end of the high-frequency generator is connected to the electrode located on the end of the capillary to which the bulb is welded. Such an arrangement of the electrodes allows to implement the case that at a certain value of voltage of the exciting generator the electrical discharge is located only between the electrodes, in the capillary, and doesn't penetrate into the bulb. The drop of the metal mercury 12 is placed in the bulb. The drop is retained in the bulb by maintaining the temperature of the latter at a lower value than the temperature in the capillary, or a so-called cold spot is formed in the bulb, i.e. a very small area of the bulb is locally cooled where all mercury is condensed.

The signal processing block 9 contains amplifiers and detectors selecting signals at the modulation frequency and at direct current. After analog-to-digital conversion these signals come to the microprocessor for further signal processing, formation of an analytical signal and display of the measured mercury concentration in the analytical cell.

Figure 2:
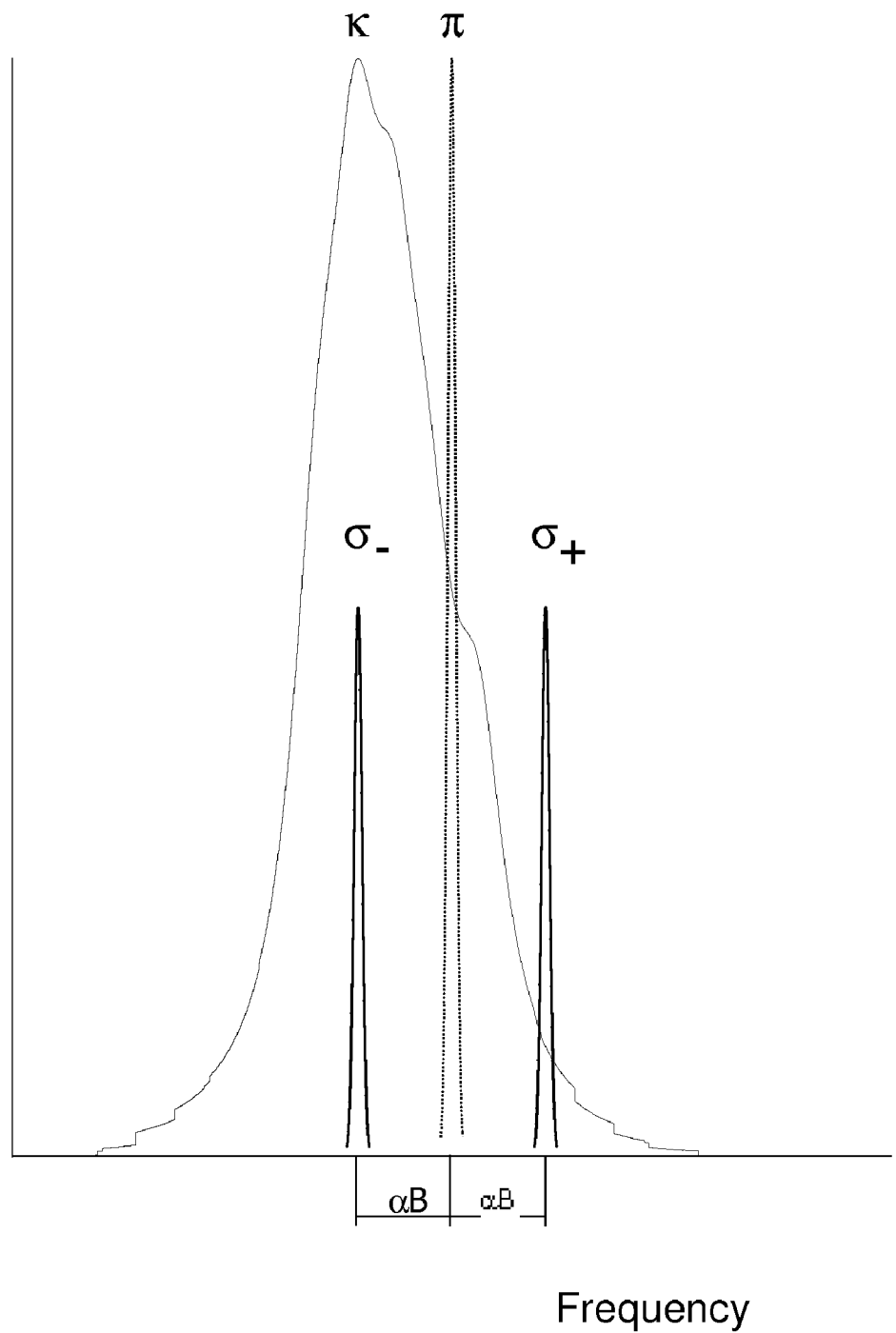
FIG. 2. Chart of spectral location of Zeeman components of the emission line of $^{198}$Hg and the envelope of the mercury absorption line (atmospheric pressure), λ=254 nm.

Let us consider the analyzer operation with the example of application of a spectral lamp with $^{198}$Hg isotope. The spectral position of its resonance emission line doesn't coincide with the spectral position of the envelope's maximum of the absorption line. In the magnetic field of magnet 3 the emission resonance line of mercury $\lambda=254$ nm splits into the unshifted $\pi$-component and two shifted $\sigma$-components (FIG. 2). Observing radiation of the spectral lamp 1 along the lines of magnetic force $\sigma_+$- and $\sigma_-$-components are observed with circular polarization clockwise and counterclockwise, respectively. The strength of the magnetic field is chosen so that the $\sigma$-component is shifted into the area of the maximum absorption of mercury atoms and thus plays the role of the analytical line while the $\sigma_-$-component is at the edge of the absorption line envelope and plays the role of the reference line. To separate the intensities of $\sigma_+$- and $\sigma_-$-components in time the optical-acoustic modulator 4 and the linear polarizer 6 are used. In absence of mercury atoms in the analytical cell 7 the intensities of $\sigma_+$- and $\sigma_-$-components are practically equal. When absorbing atoms appear, the intensity of the $\sigma_+$-component is reduced since its spectral position coincides with the maximum of the envelope of the mercury absorption line in the air while the intensity of the $\sigma_-$-component remains practically the same as it is at the edge of the absorption line envelope. As a result at the modulation frequency it is appeared the signal $S_1$ related with mercury concentration in the analytical cell. To provide selectivity the signal $S_0$ is used as the normalization signal being proportional to the direct-current component of the photo detector 8. The signals $S_1$ and $S_0$ are selected in the signal processing block 9 and the signal $S=S_1/S_0$ is calculated. The concentration of mercury atoms in the analytical cell C is related with the received signal S in the following way [1]:

$$C = -\frac{b}{2\Delta QL} \ln((b-S)/(b+S)) \qquad (1)$$

where $\Delta Q$—the differential cross section of radiation absorption of $\sigma_-$- and $\sigma_+$-component, L—the length of the analytical cell, b—the normalization constant depending on the parameters of the analyzer.

Figure 3:
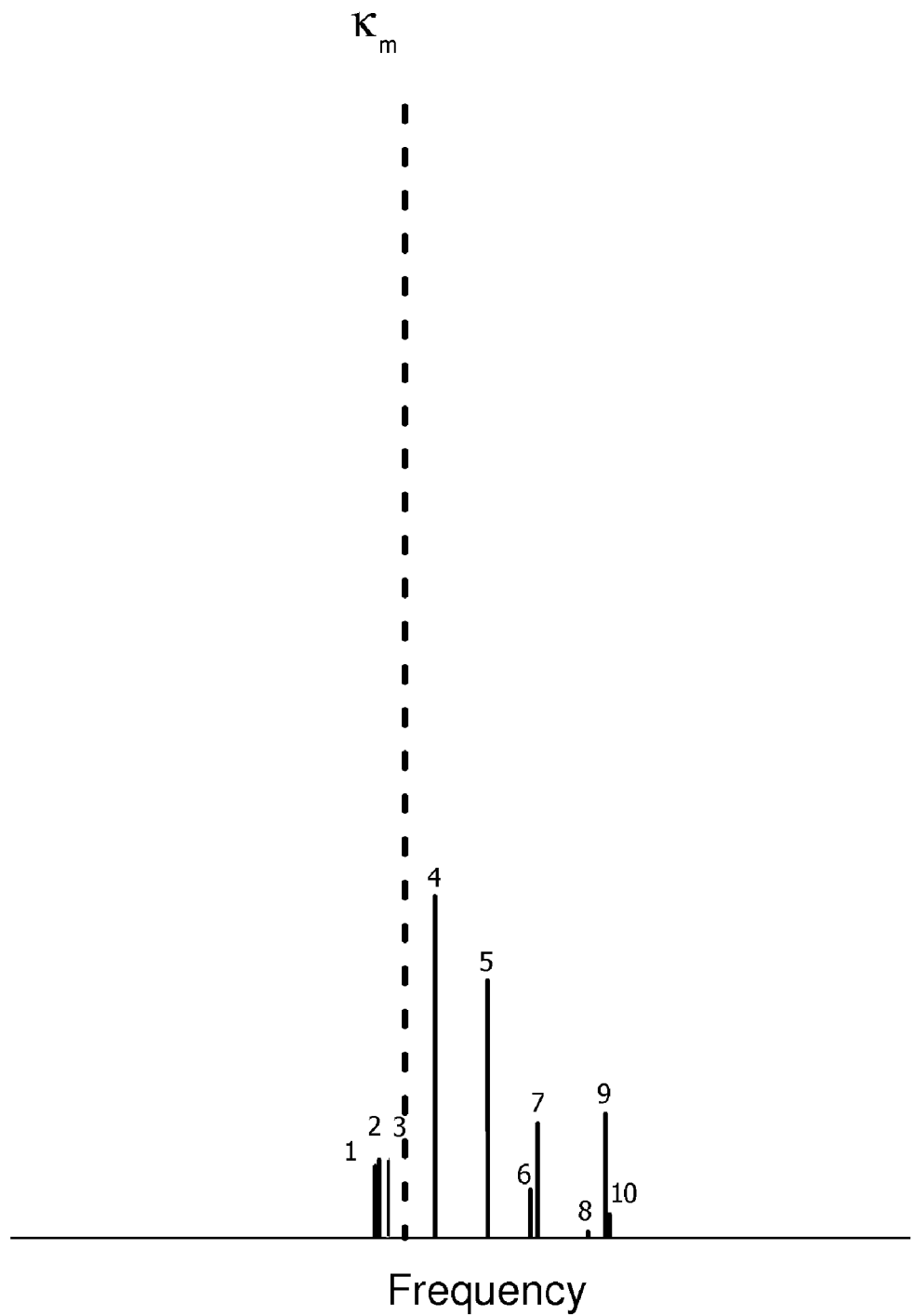
FIG. 3. Hyperfine structure of the mercury emission line λ=254 nm and location of maximum of the absorption line envelope $K_m$ at atmospheric pressure. The location of hyperfine components [2]: 1—199A, 2—204, 3—201a, 4—202, 5—200, 6—201b, 7—198, 8—196, 9—199B, 10—201c.

It follows from the formula (1) that the sensitivity at the constant length of the analytical cell is determined by the differential cross section of absorption of resonance radiation. As mercury consists of 7 stable isotopes (FIG. 3), the differential cross section can be changed by choosing a certain isotope composition of mercury used in the spectral lamp and by the value of the applied magnetic field. Table 1 shows maximum values of the relative differential cross section of absorption for different isotope composition of mercury in the source of radiation obtained by calculation.

TABLE 1

| Isotope composition | Maximum relative differential cross section, $\Delta Q/Q_{202}$ |
|---|---|
| $^{204}$Hg | 0.68 |
| $^{202}$Hg | 0.26 |
| $^{200}$Hg | 0.56 |
| $^{198}$Hg | 0.96 |
| $^{196}$Hg | 1.00 |
| Natural mixture | 0.21 |

As odd isotopes of mercury have hyperfine components located on both sides relative to the maximum of the absorption line envelope, it is obvious that the differential cross section with longitudinal geometry (when the radiation is observed along the lines of magnetic force) for them is small. The provided data show that the differential cross section achieves the maximum value with use of the monoisotope mixture with $^{198}$Hg and $^{196}$Hg, and these values are 5 times higher than the maximum differential value implemented for mercury with natural composition.

The mercury enrichment rate should not be lower than 50%; otherwise the differential cross section of absorption decreases. For example, if mercury contains 50% of $^{198}$Hg and 50% of $^{204}$Hg, the calculation shows that the value of the maximum differential cross section drops 2.5 times compared to the monoisotope $^{198}$Hg and approaches the value of the maximum differential cross section for mercury with natural composition.

To determine the detection limit DL we will use the linear approximation of the formula (1) since $S=\sigma<<b$:

$$DL = \frac{3}{\Delta QL}\sigma \qquad (2)$$

where $\sigma$—the root-mean-square deviation of the noise level of the analytical signal. The formula (2) shows that the increase of the value of the differential cross section of absorption due to application of the monoisotope $^{198}$Hg in the spectral lamp allows to decrease the detection limit in 5 times compared to use of mercury with natural composition in the spectral lamp.

Figure 4:
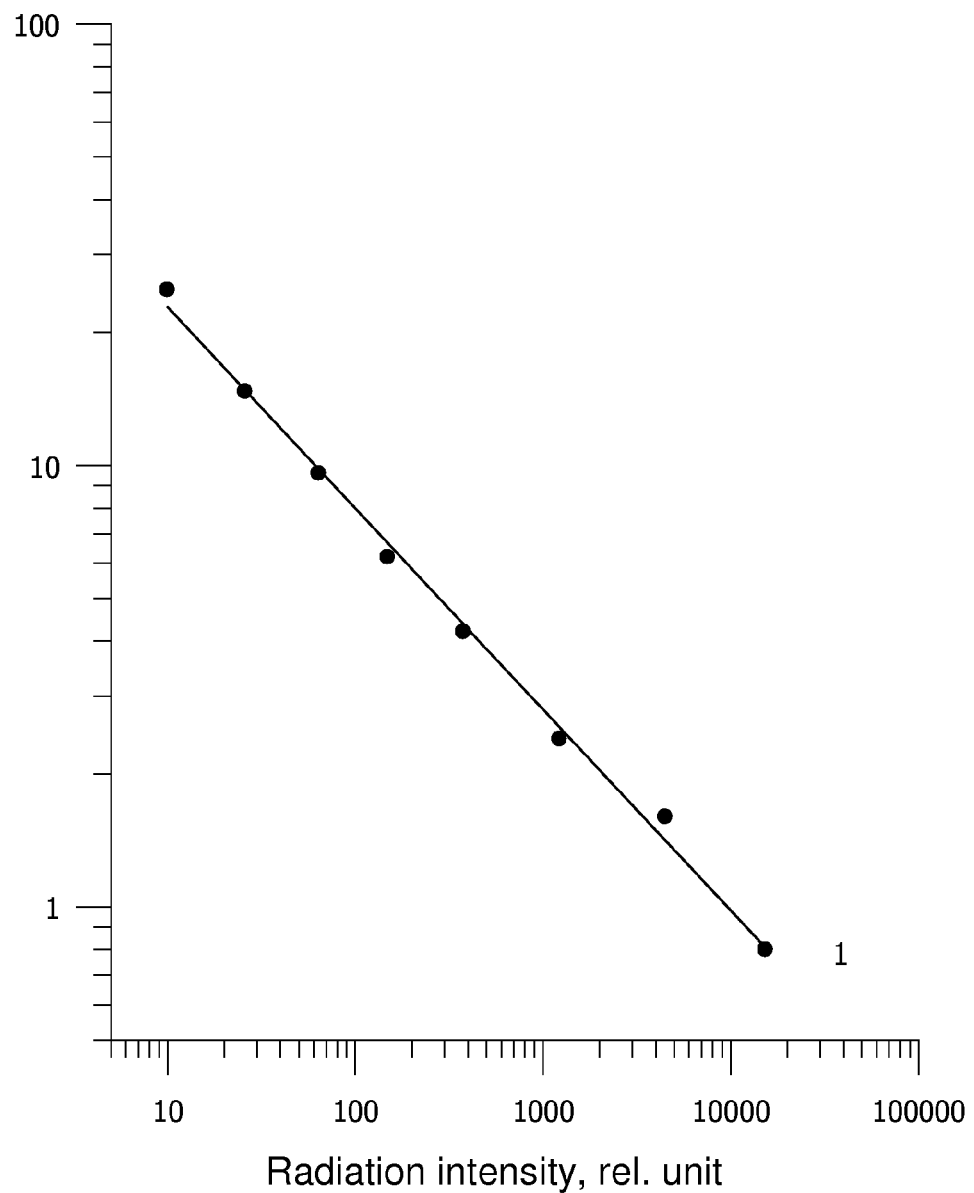
FIG. 4. Dependence of the noise level on intensity of the detected radiation.

Another way to decrease the detection limit is to reduce the noise level of the analytical signal. In our case the dominant is the shot noise determined by the detected intensity of resonance radiation. This is confirmed by FIG. 4 that shows dependence of the noise level from the detected intensity I. It shows that up to the working values of intensity the dependence takes the form of $$\sigma \sim \frac{1}{\sqrt{I}}.$$

Consequently, increased intensity of the radiation source will allow to decrease the detection limit. With the use of spectral lamps with a different buffer gas (Ar, Kr, Xe) it was experimentally received that with the same power of the exciting generator the radiation intensity is 1.5 and 4 times higher for spectral lamps using Kr and Xe as the buffer gas, respectively. Thus, the use of Xe as the buffer gas allows to decrease the detection limit twice.

Increasing of differential cross section of absorption also reduces the zero-level drift. In the analyzer the zero-level drift is basically determined by the change of the initial relation of intensities of the σ-component that is first of all is caused by temperature changes. Let the value of the zero-level drift of the analytical signal S be δ 1/° C. The value of the drift of concentration $\Delta C_d$ at all real changes of the temperature $\Delta T$ between two successive procedure of the zero test is much less than the normalization constant b, i.e. δΔT<<b. In this case we will use the linear approximation of the formula (1) and then we will get for the concentration drift:

$$\Delta C_d = \frac{\delta \Delta T}{\Delta QL} \qquad (3)$$

The formula (3) shows that five-fold increase of the differential cross section of absorption results in the respective reduction of the value of the zero-level drift of concentration.

Another way to reduce the influence of the temperature drift of the radiation source is stabilization of the concentration of mercury atoms in the gas phase inside the spectral lamp. In this case the value of self-absorption of resonance radiation and the process of transfer of radiation from different parts of the spectral lamp are stabilized. There are two processes of transition of mercury atoms from the liquid phase (from a drop of metal mercury placed inside the spectral lamp) to the gas phase: this is evaporation and sputtering in the discharge. While the evaporation process can be stabilized by maintaining a stable temperature of the drop of metal mercury, the sputtering process depends on the electrical parameters of the discharge, on the surface where mercury is placed as well as on the processes of redeposition. Therefore, partition of the evaporation zone where the drop of metal mercury is located and the discharge zone to which the exciting field is applied excludes the process of sputtering from the ways of entry of mercury atoms into the gas phase. The evaporation zone and the discharge zone are separated by means of a special design of the lamp and a certain arrangement of the electrodes. The spectral lamp consists of two parts (FIG. 5): a capillary where the discharge is actually excited and the bulb with the metal mercury drop where the temperature is maintained at a lower value than the temperature of the capillary and where no discharge is present.

Secondly, such embodiment allows to use the bulb as a reservoir of mercury vapor with the concentration determined by the temperature of the drop that compensates for mercury losses in the capillary due to sorption processes by walls of the capillary and oxidation of atomic mercury in the discharge. Absence of the bulb results in non-uniform and unstable distribution of atomic mercury along the capillary, which results in additional noises of the radiation source. In fact, a metal mercury drop is always covered with an oxide film. It does not change the value of the pressure of the saturated vapor but the exchange between the liquid and gas phases that actually leads to establishment of the pressure of saturated vapor above the drop at the given temperature slows down considerably. In these conditions the concentration of atomic mercury in the capillary is not determined by the pressure of saturated vapor but rather defined by a certain established value of the concentration determined by the processes of the atomic mercury leaving the gas phase due to sorption and oxidation in the discharge and entry of mercury atoms from the metal drop. As the parameters of the film and the processes of sorption and oxidation are non-stationary, the established distribution of atomic mercury along the capillary is not stationary either, which results in additional noises of the radiation source.

Thirdly, shaping of the excitation zone in the form of a fine capillary allows, firstly, to reduce the influence of self-absorption processes on the measurement results due to the small thickness, and, secondly, to reduce the dimensions of the magnet, which decreases its weight and, accordingly, the cost of the magnet.

Thus, this invention allows to decrease the detection level and to reduce the drift value due to the fact that mercury placed in the spectral lamp is enriched with a mercury isotope with an even number of neutrons; the spectral lamp contains a ballast cavity connected with the discharge cavity, its volume exceeding the volume of the discharge cavity, and the means of electrical discharge excitation, the discharge cavity and the ballast cavity are embodied with the possibility of exciting the discharge in the discharge cavity that does not penetrate into the ballast cavity; the spectral lamp contains Kr or Xe as the buffer gas.

LIST OF REFERENCES

1. Ganeev, A. A., Sholupov, M. N., Slyadnev, M. N. Zeeman modulation polarization spectroscopy as a variant of atomic absorption mercury analysis: opportunities and restrictions. —ZhAKh, 1996, v. 51, N8, pp. 855-864.
2. K. G. Kessler. Some experiments with Zeeman shifted levels. Physica. —1967. V. 33. P. 29-46.

The invention claimed is:

1. An atomic absorption mercury analyzer including an optically coupled photo detector, an analytical cell, a modulator of radiation polarization and a spectral lamp containing a discharge cavity located between magnet poles and connected with a means of electrical discharge excitation, with buffer gas and mercury placed into the spectral lamp, wherein the mercury placed in the spectral lamp is enriched with a mercury isotope with an even number of neutrons and atomic weight either 198 or 196, this isotope making at least 50% of the total quantity of mercury in the spectral lamp, wherein the discharge cavity in the spectral lamp is made in a form of a capillary and is connected with a ballast cavity made in a form of a bulb with the volume exceeding the volume of the discharge cavity, with the means of electrical discharge excitation, the discharge cavity and the ballast cavity embodied with the possibility of exciting a discharge in the discharge cavity that does not penetrate into the ballast cavity.

2. The atomic absorption mercury analyzer according to claim 1 wherein the buffer gas contains at least 50% of inert gas, atomic nucleus of that has the charge of at least 36.

3. The atomic absorption mercury analyzer according to claim 1, wherein the means of electrical discharge excitation is implemented as at least one electrode installed on the capillary of the spectral lamp and connected with a high-frequency exciting generator.

* * * * *